(12) United States Patent
Vorage et al.

(10) Patent No.: US 8,337,867 B2
(45) Date of Patent: Dec. 25, 2012

(54) METAL LACTATE POWDER AND METHOD FOR PREPARATION

(75) Inventors: Marcus J. A. W. Vorage, Balloo (NL); Martijn Janissen, Amsterdam (NL)

(73) Assignee: Purac Biochem B.V., AC Gorinchem (NL)

( * ) Notice: Subject to any disclaimer, the term of this patent is extended or adjusted under 35 U.S.C. 154(b) by 484 days.

(21) Appl. No.: 12/320,883

(22) Filed: Feb. 6, 2009

(65) Prior Publication Data
US 2009/0202448 A1 Aug. 13, 2009

Related U.S. Application Data

(60) Provisional application No. 61/006,981, filed on Feb. 8, 2008.

(51) Int. Cl.
*A61K 9/00* (2006.01)
*A61K 9/14* (2006.01)

(52) U.S. Cl. .................. 424/400; 424/421; 424/489

(58) Field of Classification Search .............. None
See application file for complete search history.

(56) References Cited

U.S. PATENT DOCUMENTS 3,630,775 A * 12/1971 Winkler ............ 127/71
4,282,385 A    8/1981 Metz et al.
5,274,152 A * 12/1993 Carmody ............ 556/183
6,962,006 B2 * 11/2005 Chickering et al. ........... 34/360
7,459,575 B2 * 12/2008 Klein et al. ............ 556/183
2003/0068424 A1* 4/2003 Cruz et al. .............. 426/588
2007/0149423 A1* 6/2007 Warr et al. .............. 510/101

FOREIGN PATENT DOCUMENTS

NL    07106959    * 11/1972
WO    WO 2006005754 A1 * 1/2006

OTHER PUBLICATIONS

U.S. Appl. No. 61/006,980, filed Feb. 8, 2008, Vorage et al.

* cited by examiner

*Primary Examiner* — Robert A. Wax
*Assistant Examiner* — Olga V Tcherkasskaya
(74) *Attorney, Agent, or Firm* — Oliff & Berridge, PLC (57) ABSTRACT

The present invention relates to a method for the preparation of a new metal lactate powdery product and to the resulting product itself with new properties. The metal lactate powder of the present invention is made via spray-drying and has a higher flowability, is less sticky and dusty, has an improved dissolution rate and is very suited for tabletting purposes. The invention is also directed to product applications in which said spray-dried metal lactate product may be applied, wherein the metal is selected from zinc and magnesium.

14 Claims, 4 Drawing Sheets

SEM picture obtained via the scanning electron microscope technique of spray-dried magnesium lactate powder according to the present invention.

Figure 1: SEM picture obtained via the scanning electron microscope technique of spray-dried magnesium lactate powder according to the present invention.

Figure 2: SEM picture of commercially available magnesium lactate powder.

Figure 3: SEM picture obtained via the scanning electron microscope technique of spray-dried zinc lactate powder according to the present invention (sample ZnL-slurry SC10-CL-FR-120).

Figure 4: SEM picture of commercially available zinc lactate powder (PURAMEX ZnL®; x750).

METAL LACTATE POWDER AND METHOD FOR PREPARATION

The present invention relates to a new method for the preparation of a metal lactate powdery product and to the product itself. Further, the invention is directed to product applications in which said metal lactate product may be applied.

Metal lactates such as zinc lactate or magnesium lactate are known to be prepared via crystallization. A crystallization process is a costly and complex process. Crystallization processes require several liquid/solid-separation steps for separation of the crystals. The crystals further are treated in several wash- and drying steps. Additional processing steps are needed for treating the mother liquid and the various purge streams that are a result hereof. In all these steps the risk of potential product losses and yield losses is very high making the crystallization process complex and costly.

The crystallization process itself is known to be very difficult to control. This leads to a crystalline product that does not always have very favorable properties for the applications in which it is to be used. There is for example a need for zinc lactate and magnesium lactate having improved flowability and dissolution properties. Further, crystalline zinc lactate and magnesium lactate are relatively sticky and dusty. These unfavorable properties lead to practical and safety problems in handling and transporting of the crystalline product. Further, significant amounts of products are lost in these operations as much product stays behind. It further requires additional expensive and time-consuming processing steps for cleaning the equipment and transport/packaging systems used.

There is thus a need for lactates of these metals having improved physical properties towards properties such as e.g. dissolution behavior, dustiness, flowability and an improved stability. A solution to this problem was now found by preparing these metal lactates to obtain powder or agglomerated powder in a new manner.

The present invention provides a new method for the preparation of metal lactate comprising a spray-drying process. The new spray-drying method has various advantages in comparison to above-mentioned production method of crystallization. The new production method is very efficient, has a high product yield, has minimal product losses and low production costs and does not generate waste byproducts in contrast to precipitation/crystallization processes. Further, in the new production method according to the present invention no auxiliary materials are needed such as catalysts or washing agents as e.g. ether and no separation, washing, drying or other processing steps are needed that are commonly present in crystallization processes.

The new production method is not complex and easy to (automatically) control and as a consequence a product of constant quality is achieved.

It is known to manufacture calcium lactate via spray-drying. This is about the only lactate product for which spray-drying is known to lead to a desired product.

US 20030068424 for example, refers to a Dutch patent application NL7106959 wherein a spray-drying process for sodium lactate is described. However, as confirmed by US 20030068424, this spray-drying process of sodium lactate results in a glassy product that is formed on the wall of the spray-tower. It takes special measurements, such as e.g. cooking a salt solution first after which the sodium lactate solution may be spray-dried, to prevent this product from adhering to the wall of the spray-tower. Further, the resulting product is not very stable. These problems are also known to occur when potassium lactate is spray-dried. A component such as iron lactate can also not be made via spray-drying due to the various side reactions that occur as iron is reacting with the material of which the spray-tower is made.

This demonstrates how the success of a spray-drying process and the resulting powder and its properties is dependent on the component that is to be manufactured via spray-drying and in particular on the cat-ion of said component. It is yet unknown to make magnesium or zinc lactate via spray-drying.

With the spray-drying process according to the present invention a new metal lactate powdery product is obtained having improved properties due to its new structural characteristics. These improved properties make the product easy to handle and transport unlike the present commercially available non-spray-dried metal lactate powders. Product losses in handling, transporting and packaging the powders are minimized and no additional cleaning of equipment and transport systems is necessary.

Further, as the product properties of the spray-dried product according to the present invention can be controlled, the product can be steered to have the properties that are of interest for a certain specific application. This broadens the field of possible applications in which up to now it was not possible or not very advantageous to use zinc or magnesium lactate. Further, the dustiness or stickiness of the spray-dried metal lactate powder can be controlled or steered.

Furthermore, spray-dried metal lactate according to the present invention was found to be much more suited for tabletting in contrast to commercially available metal lactate such as zinc lactate and magnesium lactate made via crystallization as the compressibility of the metal lactate of the present invention is much lower indicating that a significant lower pressure is needed to obtain firm tablets.

The spray-drying method according to the present invention for the preparation of spray-dried metal lactate comprises a spray-drying process wherein a feed solution or slurry comprising metal lactate is atomized and the atomized droplets are contacted with heated gas resulting in the formation of solid spray-dried metal lactate followed by the separation of the solid particles from the gas, wherein the metal is selected from zinc and magnesium.

The feed solution or slurry can comprise between about 10 to 70 wt % of metal lactate. When referring to solutions, a concentration range of about 10 to 45 wt % is applicable.

The spray-drying process can take place in the various well-known commercially available spray-drying equipment and apparatus in which the heated gas and the atomized metal lactate solution or slurry flow co-currently, counter-currently, as a mixed flow in the dryer, etcetera.

The heated gas, e.g. air, may have a temperature ranging from 100 degrees Celsius to about 300 degrees Celsius and/or a reduced pressure of between 0.1 to 10 mbar below atmospheric pressure and more preferably 0.5 to 5 mbar below atmospheric pressure [i.e. 0.995-0.9995 bar). The heated gas is used for the evaporation or the drying of the sprayed droplets. The drying process may be performed in one stage, meaning in one pass through the dryer, or in multiple stages.

The nozzles, through which the solution or slurry is pumped and atomized, may be located at the top, at the bottom or sideways in the dryer. Different types of nozzles are possible. In a preferred embodiment of the present invention, the nozzles are located at the top and the heated air is introduced mainly from above to flow co-currently with the spray of droplets.

The atomization may be performed by using rotary atomizers, high-pressure nozzles or two-fluid nozzles, or combinations thereof, all types of nozzles well-known to the skilled person. It was found that magnesium lactate solutions and slurries are best atomized with two-fluid nozzles and the use of compressed steam, whereas zinc lactate is preferably atomized with high-pressure nozzles at pressures of about 80 to 250, more preferably 100 to 200 bar.

The spray-dried metal lactate solution or slurry that is used as feed for the spray-drying process may be obtained by various means such as for example by means of reaction or crystallization/precipitation.

The spray-dried metal lactate feed solution or slurry may be for example obtained via reaction of an aqueous lactic acid solution with metal hydroxide or metal oxide powder or suspension in the presence of water.

In a preferred embodiment of the present invention a slurry is obtained comprising crystals which undergo a milling step before the slurry is fed to the spray tower. This way a slurry may be obtained having a certain desired particle size distribution and comprising somewhat more nicely shaped particles compared to the earlier-made crystals.

An even better result is obtained when this milling step is integrated with the crystallization step.

An other preferred embodiment of the present invention comprises a preparation of the feed stream solution or slurry to the spray-tower wherein said preparation comprises the mixing of water, lactic acid and the relevant metal hydroxide or oxide under turbulent conditions with respect to the flow profile in which the neutralization reaction takes place very fast and nucleation takes place at supersaturation conditions. The result is a highly supersaturated meta-stable solution that is directly fed to a crystallizer wherein further crystal growth takes place. The stable crystal slurry coming out of this crystallizer is then fed to the spray-tower.

The supersaturated solution may also be fed directly to the spray-tower instead of a crystallizer.

The turbulent flow profile conditions and mixing means may be achieved by using a vortex mixer or similar piece of equipment wherein the mixing means are achieved by manipulation of the direction and sizes of the flows introduced in the equipment and by the geometry of said equipment. This process or method for obtaining a supersaturated solution of metal lactate is described in detail in European patent application nr. 08101405.2 titled "Vortex mixer and method of obtaining a supersaturated solution", which is hereby incorporated as reference.

It is preferred that the pressure in the vortex mixer is at least 0.3 bar (above atmospheric pressure), preferably at least 0.5 bar. Thus, the time required for the crystals to reach a desired particle size distribution, typically by collecting the supersaturated solution in a stirred vessel or crystallizer, is reduced significantly. Of course, the pressure is limited by the mechanical strength of the mixer used, e.g. to 5 or 10 bar.

It was found that at the outlet of the vortex mixer highly supersaturated solutions with very high dry solids content, e.g. more than 25 wt % or more than 30 wt % and e.g. up to 50 wt %, can be produced when still at low viscosity. A benefit of the vortex mixer in this case is that mixing takes place before a slurry containing large amounts of small crystals is formed. These slurries containing large amounts of small crystals are well known for their high viscosities at high dry solids concentrations. Mixing of liquids at low viscosity is much faster and less energy consuming than mixing of high viscosity liquids or slurries. Thus, by using the vortex mixer, it is possible to produce slurries with very high dry solids concentrations which will be difficult if not impossible to obtain in a stirred tank reactor configuration.

Due to this preparation step before the actual spray-drying step the result of the spray-drying process according to the present invention is a powder that is very stable and has very advantageous properties with respect to for example particle size distribution (sizes in the range of about 5 to 100 µm), flowability, dissolution, dustiness and stickiness. Further, this preparation makes it possible to spray-dry highly concentrated slurries of between 10 to 70 wt % of metal lactate, more preferably between 10-45 wt %. The high through-put achieved in this way and the saving of an additonal milling step yield a significant reduction in costs of the spray-drying process.

Good results were obtained with a zinc lactate feed stream comprising particles having an average size ($d_{50}$(µm)) of about 5 to 50 µm and particular good results were obtained with a zinc lactate feed stream comprising particles having an average particle size of between 5 and 25 µm. The new powders obtained after spray-drying demonstrated for example a very good dissolution rate and flowability which made the powders very suitable for various applications, in particular in those applications where said properties play a role, such as e.g. in cosmetic and personal care applications, including oral care applications, and in controlled release applications.

Similar results were found for magnesium lactate.

In a preferred embodiment of the spray-drying process according to the present invention, the sprayed droplets are falling down while being dried by the heated air. After this first drying stage the particles may be taken through a second drying stage that may be integrated in the bottom section of the spray tower. Said bottom section then comprises an integrated bed through which heated air flows for further drying of the particles. This drying step may also be performed externally in separate drying equipment.

The particles are after the first and/or second drying step subsequently further transported via a shaking or vibrating bed. This shaking or vibrating bed serves for further conditioning as e.g. cooling down of the particles. The particles then may be taken through a classification system comprising sieves and mills if more fine-tuning of the particle size is required. The fines after milling may be recycled back to the spray section of the spray tower.

It is a further objective of the invention to provide new metal lactate products. The method yields a metal lactate product, such as zinc lactate and magnesium lactate, that is free-flowing, (controllably) less dusty and less sticky and which comprises nicely almost round shaped or spherical particles in contrast to the commercially available spray-dried metal lactate products. These latter products comprise particles with many edges looking more like cubical and pyramid shaped blocks or of a form in between. These rod- or cubical-shaped particles are an indication that said particles are made via crystallization processes. The nicely spherical-shaped spray-dried metal lactate particles of the present invention have a much narrower particle size distribution compared to commercially available metal lactate. Particles sizes may be steered and may be between 5 and a 1000 micrometer. Dependent on the application in which the metal lactate is to be used, the particles may be given the appropriate particle size distribution.

The new metal lactate product of the present invention has new structural characteristics which result in a very high flowability and an already visibly observable less dusty metal lactate product than commercially available metal lactate powder. The metal lactate powdery product of the present invention has a Hausner ratio (a well-known parameter to express or indicate the degree of flowability with) of maximally 1.18. This means that it is easier to transport and to handle and the caking tendency is less than with commercially available metal lactate. Zinc lactate made via the spray-drying method according to the present invention demonstrated a Hausner ratio of about 1.18. A Hausner ratio of higher than 1.4 means, as known to the person skilled in the art of powders, that the powder is cohesive and thus more difficult or even not suited for proper handling and transport. Commercially available zinc lactate has a Hausner ratio of about 2. Zinc lactate made via spray-drying using two-fluid nozzles demonstrated a Hausner ratio of 1.14 and zinc lactate made via spray-drying using high pressure nozzles even showed to have a Hausner ratio of 1.09. Magnesium lactate made via the spray-drying method according to the present invention has a Hausner ratio of 1.13 which indicates a good flowability in contrast to commercially available magnesium lactate made via crystallization which was measured to have a very poor flowability represented by a Hausner ratio of 1.62.

The metal lactate powders obtained via the spray-drying method according to the present invention further have a compressibility of 12% and lower to even about 8% (both for zinc lactate and magnesium lactate powder). This low compressibility factor demonstrates the suitability of the metal lactate powders of the present invention for amongst others tabletting. Commercially available zinc lactate has a compressibility of about 50%. Commercially available magnesium lactate also demonstrated a very poor compressibility of about three times higher (38%) than magnesium lactate made via the spray-drying method according to the present invention.

Further, the spray-dried metal lactate powders (both magnesium lactate and zinc lactate) of the present invention have an angle of repose and an angle of spatula of respectively 37 degrees and lower and 40 to even 34 degrees and lower. Both angles are a means to express the flowability of the powder with. As the person skilled in the art of powders is well aware of, the smaller or steeper these angles are, the better the flowability of the powder is. An angle of repose of below 40 degrees and below 45 degrees for the angle of spatula indicates a good flowability. An angle of spatula of 34 degrees or lower even indicates a fairly good to very good flowability. Commercially available magnesium lactate has an angle of repose of 48 degrees and an angle of spatula of 82 degrees. Commercially available zinc lactate shows an angle of repose of about 60 and an angle of spatula of 88.

The new product of the present invention shows a dynamic flow rate of about 112 mL/s (and higher dependent on amongst others the particle size as the skilled person is well aware of) while commercially available metal lactate powder, such as e.g. Puramex Zn®, did not show to have any consistent and measurable dynamic flow rate as it continuously caused problems due to plugging up of the measuring device.

The spray-drying method according to the present invention has shown to produce zinc lactate powders having a dissolution time (at ambient room temperature), dependent on the size and size distribution of the zinc lactate particles, from about 50 to 100 and even from 5 to 50 seconds for about 1 wt % of spray-dried zinc lactate particles or granules in water. With commercially available zinc lactate particles or granules made via crystallization it takes about 225 to 485 seconds for 1 wt % to dissolve in water at room temperature. This significant difference creates many new applications in which commercially available zinc lactate could not or was not advantageous to be used as it did not dissolve sufficiently fast enough.

Commercially available magnesium lactate showed a two times slower dissolution rate compared with magnesium lactate made via the method according to the present invention.

Due to the advantageous powder properties mentioned above, the spray-dried metal lactate powder obtained via the present invention was found to be very suitable for various product applications such as cosmetic and personal care applications, dental or oral care applications and technical applications.

Further, the spray-dried metal lactate powder according to the present invention, and in particular the spray-dried magnesium lactate, may further be used in various products in the field of food in general, especially in vitamin and mineral supplements and in beverages.

The spray-dried metal lactate powder according to the present invention was further found to be very suited to make tablets of. This creates further new applications in which before no metal lactate powder could be used as the commercially available metal lactate powder was not suited.

The following non-limiting examples illustrate the invention.

Experiments:

First Example of Spray-Drying Zinc Lactate

A slurry feed comprising zinc lactate is made via reaction of lactic acid with zinc oxide in an aqueous environment. Optionally the feed stream is passed through a milling step.

A slurry feed comprising about 35 wt % zinc lactate with crystals of about an average 40 μm ($d_{(0.5)}$) was fed to a commercially available STORK® wide-body spray dryer with co-current flow. The solution was fed at a varying temperature of 100 to 120° C. through two-fluid type nozzles (located at the top of the tower) and atomized by means of application of steam under a pressure that was varied during the test from about 10 to 6 bar. The spray of droplets was brought in contact with heated air (mainly introduced from above in the spray dry tower) with an inlet temperature of about 165 to 200° C. The outlet temperature was about 90 to 110° C.

The spray-dried particles were collected at the bottom of the tower and transported via a shaking bed for cooling down.

The resulting spray-dried zinc lactate powders obtained in the test at 8 bar and in the test at 6 bar, hereinafter respectively referred to as ZnL slurry SC10-CL-NoFR-100 and ZnL slurry SC06-CL-NoFR-100, had an average moisture content of about 9.3 wt %. ZnL slurry SC10-CL-NoFR-100 showed the following particle size distribution: $d_{0.1}$ (μm): 15.3, $d_{0.5}$ (μm): 61.5, $d_{0.9}$ (μm): 185.8 (Span=2.77).

ZnL slurry SC06-CL-NoFR-100 showed the following particle size distribution: $d_{0.1}$ (μm): 11.9, $d_{0.5}$ (μm): 51.6, $d_{0.9}$ (μm): 131.98 (Span=2.33).

At recycling the fines discharge and fines to the nozzles, at a pressure of about 10 bar and a temperature of the feed of about 120° C., a powder was obtained demonstrating a moisture content of about 3.5% and an average particle size of about 179 to 194 micrometer. This powder, hereinafter referred to as ZnL slurry SC10-CL-FR-120, was measured to have the following particle size distribution: $d_{0.1}$ (μm): 67.4, $d_{0.5}$ (μm): 120.2, $d_{0.9}$ (μm): 203.3 (Span=1.13).

When the two-fluid nozzles were exchanged for high-pressure nozzles, a pressure was applied of about 100 bar and without application of a recycle of the fines, a powder was obtained with an average moisture content of about 2.2 to 2.8 wt %. This powder, hereinafter referred to as ZnL slurry HP100-CL-NoFR-120, showed the following particle size distribution: $d_{0.1}$ (μm): 17.5, $d_{0.5}$ (μm): 47.4, $d_{0.9}$ (μm): 107.0 (Span=1.89).

Second Example of Spray-Drying Zinc Lactate

Zinc oxide was suspended in demineralised water of about 80° C. A 92 wt % lactic acid solution was added under continuously stirring until the pH of the solution was about 5.34.

The resulting about 16 wt % zinc lactate comprising solution was fed to a spray-dry tower. The slurry was fed through high-pressure type nozzles (located at the top of the tower) and atomized (applied pressure ~100 bar). The spray of droplets was brought in contact with heated air (mainly introduced from above in the spray dry tower) with an inlet temperature of about 220-245° C. The outlet temperature was about 80-120° C.

The spray-dried particles were fed to a back-filter in which the particles and air were separated. The particles were then taken through a classification system comprising sieves and a mill.

The result was a free-flowing, visually noticeably non-dusty and non-sticky zinc lactate powder with about 3 to 4 wt % moisture content.

First Example of Spray-Drying Magnesium Lactate

A slurry feed comprising magnesium lactate is made via reaction of lactic acid with magnesium oxide in an aqueous environment.

A slurry feed comprising about 35 wt % magnesium lactate with crystals of about an average size of 42 μm ($d_{0.5}$) was fed to a commercially available STORK® wide-body spray dryer with co-current flow. The solution was fed with an ingoing temperature of about 100° C. through two-fluid type nozzles (located at the top of the tower) and atomized by means of application of steam under a pressure of about 10 bar (in a later test lowered to about 6 bar). The spray of droplets was brought in contact with heated air (mainly introduced from above in the spray dry tower) with an inlet temperature of about 165 to 200° C. The outlet temperature was about 90 to 110° C.

The spray-dried particles were collected at the bottom of the tower and transported via a shaking bed for cooling down.

The resulting spray-dried magnesium lactate powder had an average moisture content of about 14 wt % and an average particle size of 52 micrometer. The particle size distribution was as follows:

<40 micrometer: 44.8%
40-63 micrometer: 33.1%
63-100 micrometer: 19.9%
>100 micrometer: 2.2%

In some tests a recycle of fines discharge and fines was returned to the nozzles.

The powder obtained demonstrated a moisture content of about 14.7% and an average particle size of about 190 to 200 micrometer. The particle size distribution was as follows:

<75 micrometer: 5.1 to 7.6%
75-106 micrometer: 31.2 to 20.9%
106-180 micrometer: 36.2 to 34.8%
180-250 micrometer: 17.3 to 22.1%
250-425 micrometer: 9.3 to 12.8%
425-850 micrometer: 0.9 to 1.8%
>850 micrometer: 0.1%

At lowering the pressure to about 6 bar, the magnesium lactate powder obtained was more coarse.

Second Example of Spray-Drying Magnesium Lactate

A slurry comprising about 30 wt % magnesium lactate with particles of an average size of about 24 μm ($d_{50}$(μm)) was fed to a spray-dry tower. The slurry was fed through two-fluid type nozzles (located at the top of the tower) and atomized by means of application of steam under a pressure of about 8 to 10 bar. The spray of droplets was brought in contact with heated air (mainly introduced from above in the spray dry tower) with an inlet temperature of about 230-245° C. The outlet temperature was about 100 to 120° C.

The spray-dried particles were further introduced in a static bed integrated in the lower section of the tower for further drying and were subsequently transported via a shaking bed for cooling down. The particles were then taken through a classification system comprising sieves and a mill.

The result was a free-flowing, visually noticeably non-dusty and non-sticky magnesium lactate powder with an about 15 wt % moisture content.

The powder obtained has the following particle size distribution: $d_{0.1}$ (μm): 6.2, $d_{0.5}$ (μm): 57.5, $d_{0.9}$ (μm): 174.7 (Span=2.9)

Commercially available magnesium lactate, PURAMEX MgL®, has the following particle size distribution: $d_{0.1}$ (μm): 3.5, $d_{0.5}$ (μm): 34.9, $d_{0.9}$ (μm): 161.5 (Span=4.5)

SEM Photo's

Figure 1:
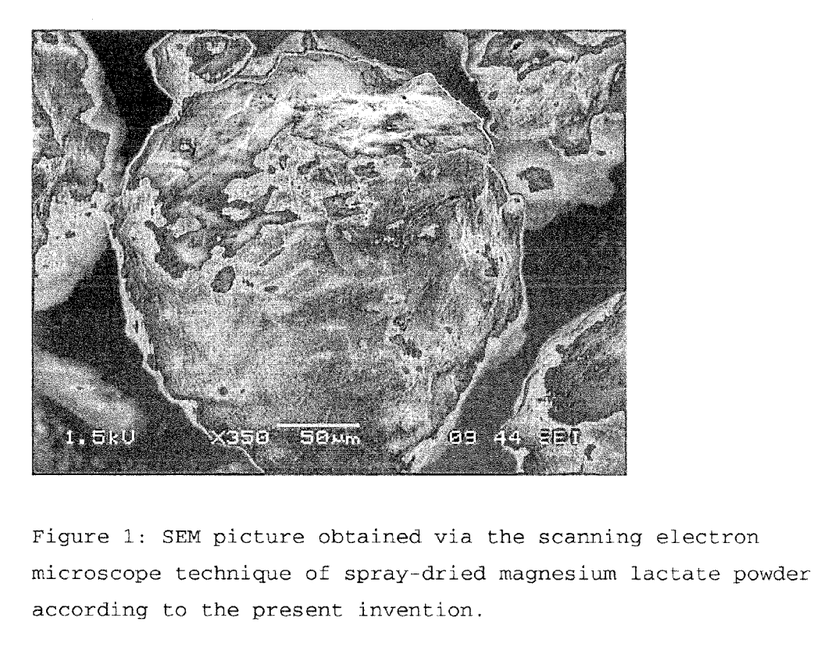
FIG. 1 is a scanning electron microscope (SEM) image of a spray-dried magnesium lactate powder according to the present invention.
Figure 2:
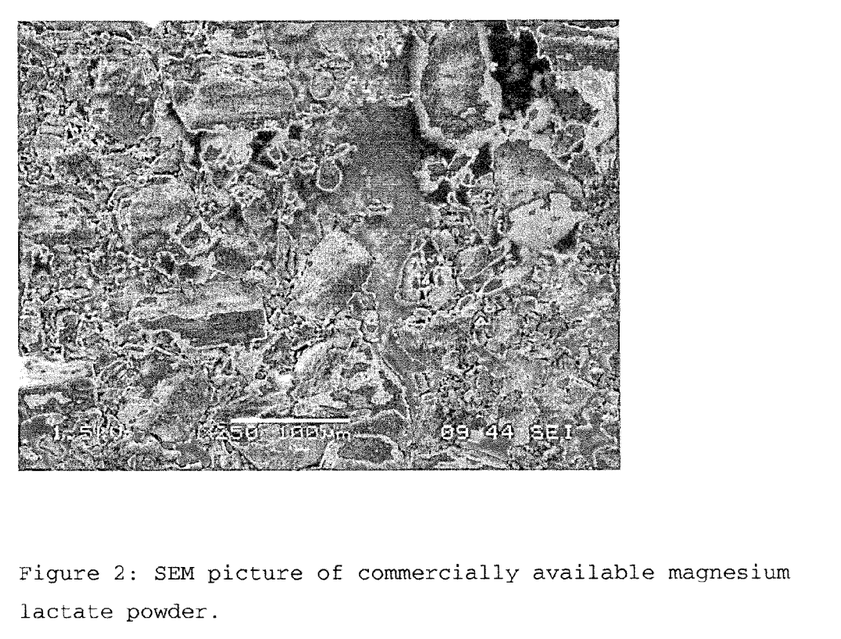
FIG. 2 is an SEM image of a commercially available magnesium lactate powder.
Figure 3:
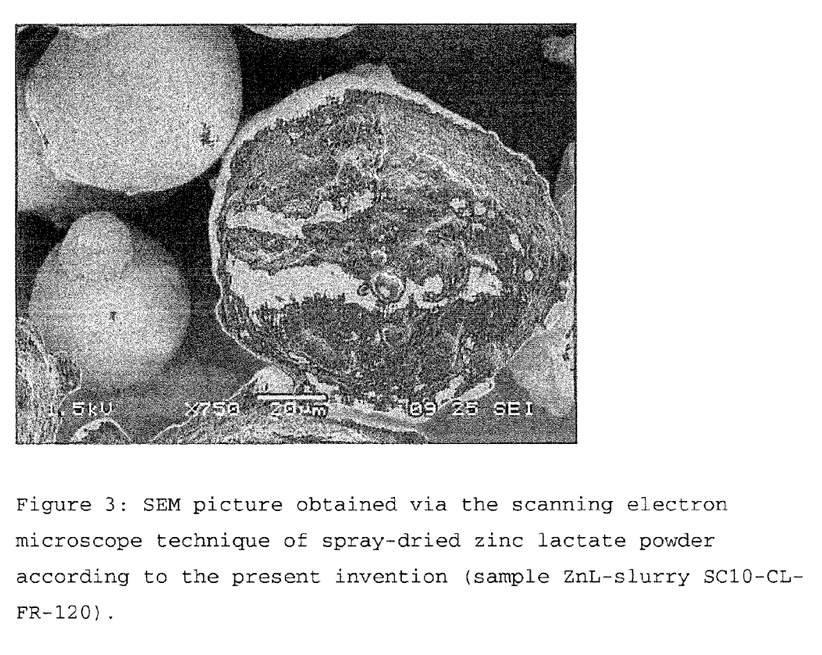
FIG. 3 is an SEM image of a spray-dried zinc lactate powder according to the present invention (sample ZnL-slurry SC10-CLFR-120).
Figure 4:
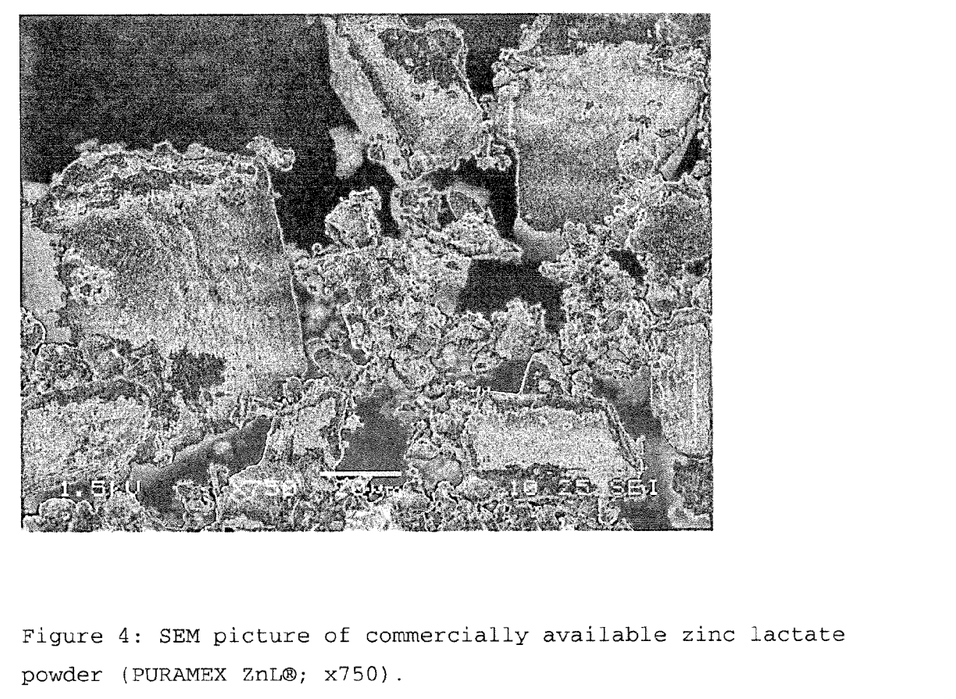
FIG. 4 is an SEM image of a commercially available zinc lactate powder (PURAMEX ZnLB; x750).

SEM pictures of the spray-dried powder compositions obtained via the method according to the present invention showed almost completely round or spherical shaped particles (some agglomerated together) as shown in FIGS. 1 (magnesium lactate) and 3 (zinc lactate) in contrast to commercially available magnesium lactate and zinc lactate powder as e.g. PURAMEX MgL® (FIG. 2) and PURAMEX ZnL® (FIG. 4), both obtained from PURAC Biochem B.V.

Measurement of the Dissolution Rate 198.0 gram of demineralised water is weighed into a 250 ml glass beaker to which a magnetic stirring bar (4 cm) is added. The beaker is placed on a magnetic stirrer and the solution is stirred at 500 rpm. The conductivity meter and thermometer are inserted. 2.00±0.02 gram (1% (w/w)) metal lactate sample is added and the conductivity is automatically measured once every 5 seconds and registered by computer. After 20 minutes the measurement of conductivity is stopped. From the conductivity measurements in time the dissolution rate is calculated using the following formula:

$$Dt = Ct/C_{end} \cdot 100$$

Wherein Dt is the dissolution rate (%) at given time (t), Ct is the conductivity (mS/cm) at given time (t), $C_{end}$ is the conductivity (mS/cm) at the end of the measurement (t).

In the initial tests it turned out that all samples dissolve readily. It is estimated that therefore all samples will be dissolved in 1200 seconds. Thus the dissolution rate is calculated with the data from the conductivity measurements using the value for the conductivity at 1200 seconds. The dissolution time is determined at 98% dissolution rate. The measured values are displayed in the following table.

TABLE 1

| | dissolution times in seconds (sec) | |
|---|---|---|
| Compound | Remarks | Dissolution time (sec) |
| Commercially available crystalline zinc lactate (fines) | PURAMEX ZnL FINE ® | 225-395 |

TABLE 1-continued dissolution times in seconds (sec)

| Compound | Remarks | Dissolution time (sec) |
|---|---|---|
| Spray-dried Zinc lactate particles (1) | 0% crystallinity | 5-50 |
| Spray-dried zinc lactate (ZnL slurry HP100-CL-NoFR-120) | 30% crystallinity | 75-85 |
| Commercially available magnesium lactate | PURAMEX MgL ® | 342.5 |
| Spray-dried magnesium lactate (2) | | 172.5 |

As the artisan in the field of powders knows, the dissolution time depends on the particle size and particle size distribution. The dissolution times measured varied therefore between powders with a dissolution time of 5 seconds to powders with a dissolution time of about 50 seconds.
(1) These zinc lactate particles were made by spray-drying the 16 wt %-comprising zinc lactate solution according to the above-described second example of spray-drying zinc lactate.
(2) These magnesium lactate particles were made by spray-drying the 30 wt % magnesium lactate feed stream according to the above-described second example of spray-drying magnesium lactate.

Measurement of the the Hausner Ratio, Compressibility, the Angle of Repose and the Angle of Spatula These are all standard measurements described in various text and hand books on powders and their properties. The various measurements were done using a Micron Powder Characteristics Tester™ (Model PT-N) from Hosokawa Micron International Inc.

The Hausner ratio is determined by measurement of the tapped and untapped (or aerated) bulk density.

Compressibility is also determined by measurement of the tapped or packed and untapped density.

The angle of repose is determined by measurement of the angle of a cone of powder that is formed by pouring the powder through a glass funnel.

The angle of spatula is determined by measurement the difference in the angle of powder—that stays behind on a spatula when a container with said spatula on the bottom of it and filled with said powder is lowered and the spatula stays on the same height—and the angle of the powder on said spatula after the spatula was tapped by a weight.

The results are summarized in the following Table.

TABLE 2

Measured properties of zinc lactate (ZnL) powders obtained via spray-drying and of commercially available zinc lactate

| Sample | Aerated Bulk Density ($kg\,m^{-3}$) | Tapped Bulk Density ($kg\,m^{-3}$) | Hausner Ratio | Carr class | Compressibility (%) | | Angle of repose (°) | | Angle of spatula (°) | | Uniformity [index] | | Flowability index | |
|---|---|---|---|---|---|---|---|---|---|---|---|---|---|---|
| | | | | | | [index] | | [index] | | [index] | | [index] | | |
| ZnL Slurry SC06-CL-NoFR-100 | 911 | 1065 | 1.17 | Good | 14.46 | 21 | 36 | 19.5 | 55 | 16 | 5.32 | 22.5 | 79 | Good |
| ZnL Slurry SC10-CL-FR-120 | 556 | 633 | 1.14 | Good | 12.16 | 22 | 37 | 18 | 34 | 21 | 1.99 | 23 | 84 | Fairly good |
| ZnL Slurry SC10-NoFR-100 | 916 | 1084 | 1.18 | Good | 15.50 | 20 | 38 | 18 | 56 | 16 | 4.94 | 22.5 | 76.5 | Good |
| ZnL Slurry HP100-CL-NoFR-120 | 805 | 878 | 1.09 | Excellent | 8.31 | 23 | 37 | 18 | 43 | 18 | 3.19 | 23 | 82 | Fairly good |
| Commerc. Available ZnL Puramex Zn ® | 828 | 1189 | 1.44 | Very poor | 30.36 | 12 | 63 | 7 | 88 | 7 | 10.15 | 18 | 44 | Not good |
| Commerc. Available ZnL Puramex Zn/Fine ® | 458 | 921 | 2.01 | Very very poor | 50.27 | 0 | 56 | 9.5 | 89 | 7 | 10.88 | 18 | 34.5 | bad |

Table 3 shows the measured values for the various parameters of magnesium lactate made via crystallization (commercially available magnesium lactate PURAMEX MgL®) and spray-dried magnesium lactate made via the method according to the present invention.

TABLE 3

Measured properties of magnesium lactate (MgL) powders

| Sample | Aerated Bulk Density (kg m$^{-3}$) | Tapped Bulk Density (kg m$^{-3}$) | Hausner Ratio | Carr class | Compressibility (%) [index] | | Angle of repose (°) [index] | | Angle of spatula (°) [index] | | Uniformity [index] | | Flowability index | |
|---|---|---|---|---|---|---|---|---|---|---|---|---|---|---|
| Commerc. Available MgL | 600 | 971 | 1.62 | very, very poor | 38.21 | 4.5 | 48 | 12 | 82 | 7 | 14.5 | 20 | 43.5 | Not good |
| Spray-dried MgL | 574 | 648 | 1.13 | Good | 11.42 | 22 | 39 | 18 | 38 | 20 | 12.2 | 20 | 80 | good |

The "Carr class" is a known index or scale (R. I. Carr, 1965, Evaluation of flow properties of solids) based on compaction and used to compare the flow properties of various powders with each other. The expressions "good" and "fairly good" on this scale indicate that the magnesium and zinc lactate powders of the present invention are very well free-flowing in contrast to the commercially available magnesium and zinc lactate powders. It further indicates that in handling and transporting the powders, e.g. packaged in big bags, the powders are not significantly compressed. As a consequence, the big bags are not suddenly "half empty" when they reach the customer.

Flowability

The flowability can also be expressed by measurement of the dynamic flow rate, which is also a well-known standardized method. The dynamic flow rate is measured by measuring the time for 600 ml of powder product to flow through a 2 cm orifice of a tube. A dynamic flow rate of or above 50 and preferably of or above 70 or 80 ml/s is acceptable in terms of the powder being suited for the normal handling and transporting activities. The higher the dynamic flow rate, the easier and more efficient, in terms of time and losses of powder that remains behind, the handling and transport of the powder will be.

The dynamic flow rate was measured to be 111.5 ml/s for ZnL Slurry SC10-CL-FR-120. The dynamic flow rate of commercially available zinc lactate (Puramex ZN Fines®) could not be measured as the zinc lactate plugged up the opening of the tube.

Compaction Behavior

The difference in compaction behavior of magnesium lactate produced via the spray drying method according to the present invention and of commercially available magnesium lactate made via crystallization was further determined by two different measurements.

Tablets were made of above-mentioned powders and in order to obtain different strength tablets, the powders were compressed with different compression forces, namely 3 kN, 4 kN and 5 kN. For the tabletting process an Instron® machine and cylindrical mould with a diameter of 10 mm were used.

The strength of these tablets was measured by measuring the dynamic fracture strength (DFS). It is measured with a Texture Analyser® using a 5 kg loading cell. Compression pressure was loaded on a cylindrical tablet, positioned at its side. The force at which the first fracture appears is measured. The results are expressed as the force at failure and are tabulated in Table 4.

TABLE 4

Dynamic fractures strengths (DFS) as function of compression force of commercially available magnesium lactate (MgL) and of spray-dried magnesium lactate (MgL) obtainable via the method according to the present invention.

| Sample | Compression Force [kN] | DFS [kPa] |
|---|---|---|
| Spray-dried MgL | 3 | 6 |
| | 3 | 5.77 |
| Spray-dried MgL | 4 | 7.02 |
| | 4 | 8.57 |
| Spray-dried MgL | 5 | 9.91 |
| | 5 | 10.49 |
| Commercially available MgL | 3 | 1.23 |
| | 3 | 1.63 |
| Commercially available MgL | 5 | 2.8 |
| | 5 | 2.67 |

The results in the Table show that the tablets made of magnesium lactate that was obtained by the spray-drying method according to the present invention have higher dynamic fracture strength values while made under the same compaction force compared to the tablets made of commercially available magnesium lactate Puramex Mg® from Purac Biochem B.V. The tablets made of the powders of the present invention are thus stronger. A higher force is needed to break said tablets.

The strength of the commercially available powder and of the powder obtainable via the method according to the present invention was measured via the well-known Kawakita test (ref. M. Celik, Overview of compaction data analysis techniques, Drug development and industrial pharmacy 18 (1992) 767). In this test, the strength of the powders is measured by application of a compression force on the powders with different powder bed heights of respectively 100, 200 and 300 mg. This was measured using an Instron® machine and the same mould as for the above-described tabletting tests, where the maximum compaction force was set up on 5 kN.

During this test the compression force as function of the displacement of the bed is obtained. From this curve the yield stress of the powder and of a single layer of powder are calculated.

TABLE 5

Yield stress values (tau) for the different powder bed heights (h) of commercially available magnesium lactate (MgL) and of spray-dried magnesium lactate (MgL) obtainable via the method according to the present invention.

| Commercially available MgL | | Spray-dried MgL | |
|---|---|---|---|
| h [mm] | tau [kPa] | h [mm] | tau [kPa] |
| 0 | 339 | 0 | 247 |
| 2.2 | 2371 | 2.2 | 2222 |
| 4.7 | 4203 | 4.7 | 3226 |
| 5.8 | 5725 | 6.5 | 5719 |

The lower yield stress value of spray-dried magnesium lactate powder of the present invention indicates better compaction properties of this material in comparison to commercially available magnesium lactate Puramex Mg® from Purac Biochem B.V.

The invention claimed is:

1. A spray-drying method for preparing a zinc lactate or a magnesium lactate product, the method comprising:
    atomizing a solution or slurry comprising zinc lactate or magnesium lactate into droplets;
    contacting the droplets with heated gas to form solid spray-dried zinc lactate or magnesium lactate particles; and then
    separating the solid particles from the gas;
    wherein the solution or slurry comprising zinc lactate or magnesium lactate is pretreated by reacting lactic acid with a zinc or magnesium oxide or hydroxide in an aqueous medium to obtain a supersaturated zinc lactate or magnesium lactate solution.

2. The method according to claim 1 wherein the heated gas is air at reduced pressure.

3. The method according to claim 1 wherein the heated gas has a temperature of between 100 and 300 degrees Celsius and/or a pressure of between 0.990 and 1 bar.

4. The method according to claim 1 wherein the solution or slurry is atomized by applying compressed air or steam and using a two-fluid nozzle, or by applying a pressure of between 80 to 250 bar in combination with using a high pressure nozzle.

5. The method according to claim 4 wherein the solution or slurry comprises zinc lactate and is atomized by applying a high pressure nozzle at a pressure of between 80 to 250 bar.

6. The method according to claim 1 wherein the solution or slurry comprises 10-70 wt % of zinc lactate or magnesium metal lactate.

7. A spray-dried zinc lactate or magnesium lactate powder obtainable by the method according to claim 1.

8. The spray-dried zinc lactate or magnesium lactate powder of claim 7 having a Hausner ratio of less than 1.15.

9. The spray-dried zinc lactate or magnesium lactate powder of claim 7 having a dynamic flow rate of at least 50 mL/s.

10. The spray-dried zinc lactate or magnesium lactate powder of claim 7 having a dissolution time of less than 100 seconds for 1 wt % of zinc lactate or magnesium lactate in water at ambient room temperature.

11. A tablet comprising the spray-dried zinc lactate or magnesium lactate powder of claim 7.

12. A personal care, cosmetic, dental, or technical product comprising the spray-dried zinc lactate or magnesium lactate powder of claim 7.

13. A food or drink product comprising the spray-dried zinc lactate or magnesium lactate powder of claim 7.

14. The method according to claim 1 wherein the supersaturated zinc lactate or magnesium lactate solution or slurry is directly fed to a crystallizer to obtain a crystal slurry that is spray-dried.

* * * * *

UNITED STATES PATENT AND TRADEMARK OFFICE
CERTIFICATE OF CORRECTION

| | | |
|---|---|---|
| PATENT NO. | : 8,337,867 B2 | Page 1 of 1 |
| APPLICATION NO. | : 12/320883 | |
| DATED | : December 25, 2012 | |
| INVENTOR(S) | : Vorage et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Eighteenth Day of November, 2014

Michelle K. Lee
*Deputy Director of the United States Patent and Trademark Office*